United States Patent
Zhang et al.

(10) Patent No.: US 7,424,089 B2
(45) Date of Patent: *Sep. 9, 2008

(54) SYSTEM AND METHOD FOR RECONSTRUCTING IMAGE BY USING STRAIGHT-LINE TRAJECTORY SCAN

(75) Inventors: Li Zhang, Beijing (CN); Hewei Gao, Beijing (CN); Zhiqiang Chen, Beijing (CN); Kejun Kang, Beijing (CN); Jianping Cheng, Beijing (CN); Yuanjing Li, Beijing (CN); Yinong Liu, Beijing (CN); Yuxiang Xing, Beijing (CN); Ziran Zhao, Beijing (CN); Yongshun Xiao, Beijing (CN)

(73) Assignees: Tsinghua University (CN); Nuctech Company Limited (CN)

( * ) Notice: Subject to any disclaimer, the term of this patent is extended or adjusted under 35 U.S.C. 154(b) by 0 days.

This patent is subject to a terminal disclaimer.

(21) Appl. No.: 11/546,717

(22) Filed: Oct. 12, 2006

(65) Prior Publication Data
US 2007/0116175 A1 May 24, 2007

(30) Foreign Application Priority Data
Nov. 21, 2005 (CN) .................. 2005 1 0123588

(51) Int. Cl.
*H05G 1/60* (2006.01)
(52) U.S. Cl. ............................. 378/4; 378/21; 378/57
(58) Field of Classification Search .................. 378/4, 378/21, 57, 901
See application file for complete search history.

(56) References Cited

U.S. PATENT DOCUMENTS 5,170,439 A * 12/1992 Zeng et al. .................. 382/131

| | | | |
|---|---|---|---|
| 6,862,337 B2 * | 3/2005 | Claus et al. | 378/26 |
| 7,245,755 B1 * | 7/2007 | Pan et al. | 382/131 |
| 2006/0039525 A1 * | 2/2006 | Bontus et al. | 378/4 |

(Continued)

OTHER PUBLICATIONS

Gao et al., Volumetric Imaging from a Multisegment Straight-line Trajectory and a Practical Reconstruction Algoritm, Optical Engineering, vol. 46(7), Jul. 2007, pp. 077004-1 to 2358.*

(Continued)

*Primary Examiner*—Courtney Thomas
*Assistant Examiner*—Alexander H Taningco
(74) *Attorney, Agent, or Firm*—Westman, Champlin & Kelly P.A.

(57) ABSTRACT

It is disclosed a system and a method for reconstructing an image by using a straight-line trajectory scan to avoid image spatial resolution reduction due to interpolations in angular direction and detector direction during data rebinning. This system comprises: a projection data conversion section for converting projection data from straight-line trajectory scan into projection data under quasi-parallel-beam scan; a filtration section for obtaining filtered projection data by convoluting the projection data under quasi-parallel-beam scan with a predetermined convolutional kernel; and a back-projection section for reconstructing an image by back-projecting the filtered projection data with a weighting factor. By using the inventive system and method, the spatial resolution in the reconstructed image is improved, and the influence of data truncation on the reconstructed image is reduced. The present invention applies the filtration and back-projection mode, and thus has general advantages of the filtration and back projection, such as simplicity and efficiency. And it is easy to be parallelized and accelerated.

12 Claims, 4 Drawing Sheets

U.S. PATENT DOCUMENTS

2006/0115040 A1* 6/2006 Chen .......................... 378/19
2007/0036418 A1* 2/2007 Pan et al. .................... 382/131
2007/0116177 A1* 5/2007 Chen et al. .................. 378/57

OTHER PUBLICATIONS

Sidky et al., Volume Image Recontruction from a Straight-line Source Trajectory, IEEE Nuclear Science Symposium Conference Record, Mar. 2005, pp. 2441-2444.*

Gao et al., An Extrapolation Method for Image Reconstruction from a Straight-line Trajectory, IEEE Nuclear Science Symposium Conference Record, 2006, pp. 2304-2308.*

Gao et al., Direct Filtered-backprojection-type Reconstruction from a Straight-line Trajectory, Optical Engineering, vol. 46 (5), May 2007, pp. 057003-1 to 057003-11.*

"An Adapted Fan Volume Sampling Scheme for 3D Algebraic Reconstruction in Linear Tomosynthesis", by P. Bleuet et al., *IEEE*, 2002, pp. 1720-1724.

"Fan-Beam Reconstruction From a Straight Line of Source Points", by B. Smith et al., *IEEE*, 1993, pp. 10-18.

Scanning of Logs with Linear Cone-Beam Tomography, by M. Magnusson et al, *Computers and Electronics in Agriculture*, 2003, pp. 45-62.

* cited by examiner (A)

(B)

(C)

(D)

(E)

(F)

SYSTEM AND METHOD FOR RECONSTRUCTING IMAGE BY USING STRAIGHT-LINE TRAJECTORY SCAN

BACKGROUND OF THE INVENTION

The present application claims priority of Chinese patent application Ser. No. 200510123588.0, filed Nov. 21, 2005, the content of which is hereby incorporated by reference in its entirety.

1. Field of the Invention

The present invention relates to the radiographic field, and more particularly to a system and method for reconstructing an image by using a straight-line trajectory scan to improve the scan speed of a three-dimension stereography.

2. Description of the Prior Art

With the development of CT (computed tomography) techniques, a tomographic image with a certain quality can be reconstructed in a case of situation where a limited angle projection data is obtained or the data is truncated. Thus, it becomes practical to apply an incomplete scan and reconstruct approximate images. Theoretically, for an imaging system with a straight-line trajectory, if the length of scanning trajectory is infinite, an exact reconstruction could be achieved. If the trajectory is of a finite length, then it is equivalent to a limited-angle CT scan. Therefore, by using CT reconstructions dealing with incomplete data, cross-section images can be obtained from a straight-line imaging system, and the stereoscopic radiography is achieved.

In practical security inspections, fast custom clearance and rotation of large object are two difficulties. This is because in conventional CT imaging systems, we need either rotate the object to be inspected, or rotate the detector and the source while the object remains stationary. That is to say, it is difficult for large volume object to be inspected such as train and truck. Besides, a circular cone-beam scan has another drawback of large cone-angle problem.

With respect to the above problems, an imaging system having a straight-line trajectory, Computed Laminography system, has already been proposed. It has a small range of projection angles and tomosynthesis kinds of reconstruction algorithms are often used. Hence it is poor in three-dimension stereoscopic imaging capability and is thus not applied in the security inspections. To reconstruct an image from a straight-line trajectory, the rebinning-to-parallel-beam algorithm is a common choice, in which, projection data from the straight-line trajectory scan is rebinned into data under parallel beam scan and then the parallel beam filtered back-projection (FBP) reconstruction is carried out. However, this algorithm has a problem of low spatial resolution. This is because when the straight-line trajectory scanned data are rebinned into the parallel-beam scanned data, interpolations in the angular direction and the detector direction are needed and could reduce the spatial resolution in reconstructed images.

SUMMARY OF THE INVENTION

In view of the above problems, the present invention is done. It is an object of the present invention to provide a system and a method for reconstructing an image from a straight-line trajectory scan. In this method, the projection data are not necessarily rebinned into parallel-beam so that the image resolution reduction due to the interpolations in the angular direction and the detector direction during data rebinning is avoid. Therefore, the image quality of the reconstruction is improved.

In one aspect of the present invention, there is provided an image reconstruction system from a straight-line trajectory scan, which comprises: a projection data conversion section for converting projection data under straight-line trajectory scan into projection data under quasi-parallel-beam scan; a filtration section for obtaining filtered projection data by convoluting the projection data under quasi-parallel-beam scan with a predetermined convolutional kernel; and a back-projection section for reconstructing an image by back-projecting the filtered projection data with a weighting factor.

Further, according to an embodiment of the present invention, the system associated with the image reconstruction further comprises a detector matrix including a plurality of detector elements for receiving transmitted signals caused by radiations which are emitted from a radiation source and penetrate through an object to be inspected, and for converting the transmitted radiations into the projection data.

Further, according to an embodiment of the present invention, the plurality of detector elements are arranged in accordance with one and the same spacing interval.

Further, according to an embodiment of the present invention, the projection data conversion section reverses and shifts the projection data $p(l,t,z)$ to obtain the projection data $q(l,t,z)$ under quasi-parallel-beam scan, wherein the projection data $p(l,t,z)$ denotes a projection value at a coordinate of t in the $z^{th}$ slice of the detector matrix when the object to be inspected relatively moves to a coordinate of l on the line; the filtration section performs one-dimension convolution of the projection data $q(l,t,z)$ under-quasi-parallel beam scan with the predetermined convolutional kernel in the l direction to obtain the filtered projection data $Q(l',t,z)$; the back-projection section back-projects the filtered projection data $Q(l',t,z)$ with a weighting factor along the radiation projection direction to obtain the reconstructed image.

Further, according to an embodiment of the present invention, the plurality of detector elements are arranged around the radiation source in accordance with one and the same angular interval.

Further, according to an embodiment of the present invention, the projection data conversion section reverses and shifts the projection data $p(l,\gamma,z)$ to obtain the projection data $q(l,\gamma,z)$ under quasi-parallel-beam scan, wherein the projection data $p(l,\gamma,z)$ denotes a projection value at an angular position of y in the $z^{th}$ slice of the detector array when the object to be inspected relatively moves to a coordinate of l on the line; the filtration section performs one-dimension convolution of the projection data $q(l,\gamma,z)$ under-quasi-parallel beam scan with the predetermined convolutional kernel in the l direction to obtain the filtered projection data $Q(l',\gamma,z)$ ; the back-projection section back-projects the filtered projection data $Q(l',\gamma,z)$ with a weighting factor along the radiation projection direction to obtain the reconstructed image.

In another aspect of the present invention, there is provided a method for reconstructing an image from a straight-line trajectory scan, comprising: a projection data conversion step for converting projection data under straight-line trajectory scan into projection data under quasi-parallel-beam scan; a filtration step for obtaining filtered projection data by convoluting the projection data under quasi-parallel-beam scan with a predetermined convolutional kernel; and a back-projection step for reconstructing an image by back-projecting the filtered projection data with a weighting factor.

Further, according to an embodiment of the present invention, the method for reconstructing an image further comprises a step of: receiving transmitted signals caused by radiations which are emitted from a radiation source and penetrate through an object to be inspected and converting the transmitted signals into the projection data by a detector matrix including a plurality of detector elements.

Further, according to an embodiment of the present invention, the plurality of detector elements are arranged in accordance with one and the same spacing interval.

Further, according to an embodiment of the present invention, the projection data conversion step reverses and shifts the projection data p(l,t,z) to obtain the projection data q(l,t,z) under quasi-parallel-beam scan, wherein the projection data p(l,t,z) denotes a projection value at a coordinate of t in the $z^{th}$ slice of the detector array when the object to be inspected relatively moves to a coordinate of l on the line; the filtration step performs one-dimension convolution of the projection data q(l,t,z) under quasi-parallel-beam scan with the predetermined convolutional kernel in the l direction to obtain the filtered projection data Q(l',t,z); the back-projection step back-projects the filtered projection data Q(l',t,z) along the radiation projection direction with a weighting factor to obtain the reconstructed image.

Further, according to an embodiment of the present invention, the plurality is of detector elements are arranged with regard to the radiation source in accordance with one and the same angular interval.

Further, according to an embodiment of the present invention, the projection data conversion step reverses and shifts the projection data p(l,γ,z) to obtain the projection data q(l,γ,z) under quasi parallel beam scan, wherein the projection data p(l,γ,z) denotes a projection value at an angular position of γ in the $z^{th}$ slice of the detector array when the object to be inspected relatively moves to a coordinate of l on the line; the filtration step one-dimension convolutes the projection data q(l,γ,z) under quasi-parallel-beam scan with the predetermined convolutional kernel in the l direction to obtain the filtered projection data Q(l',γ,z); the back-projection step back-projects the filtered projection data Q(l',γ,z) along the radiation projection direction with a weighting factor to obtain the reconstructed image.

As compared the present invention with the rebinning-to-parallel-beam algorithm, the image spatial resolution is improved, and the influence of data truncation on the reconstructed image is reduced. The present invention applies the filtration and back-projection mode, and thus has general advantages of the filtration and back projection, such as simplicity and efficiency. And it is easy to be parallelized and accelerated.

Therefore, as compared with conventional radioscopic scanner, the system according to the present invention obtains both a DR (digital radiography) image and a tomographic image, solves the problem of objects overlapping existing in the radioscopic system, and can achieve a fast stereo imaging in the security inspection fields. Compared with the conventional CT imaging system, the system according to the present invention has advantages of fast examination speed, and no rotation, and out of problems such as large cone-angle problem in circular cone-beam CT scanner.

DETAILED DESCRIPTION OF THE PREFERRED EMBODIMENTS

Hereafter, the embodiments of the present invention will be described in detail with reference to the accompanying drawings.

Figure 1:
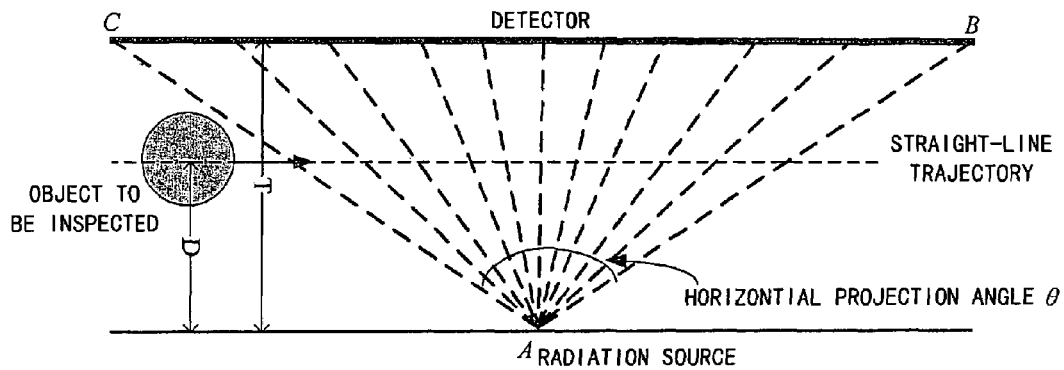
FIG. 1 is a plane diagram of a straight-line trajectory scan performed in the imaging system according to the present invention.
Figure 2:
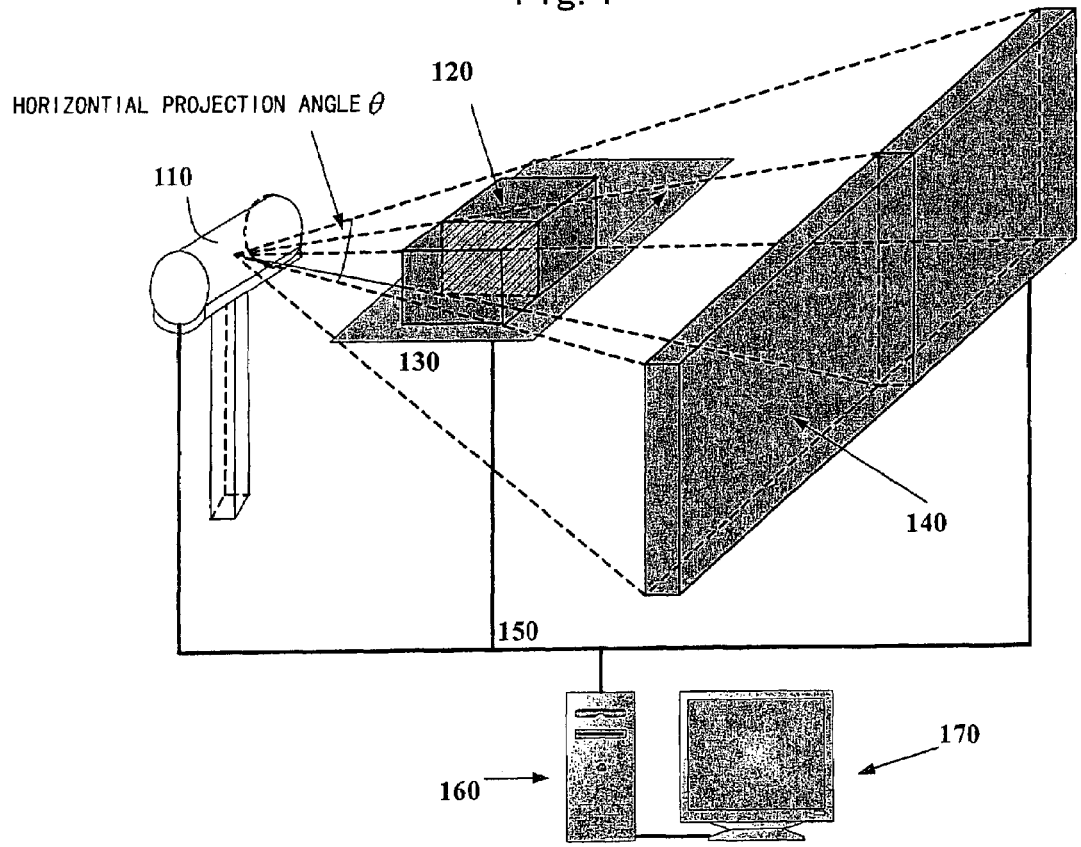
FIG. 2 is a structural diagram of the imaging system according to the present invention.

FIG. 1 is a plane diagram of a straight-line trajectory scan performed in the imaging system according to the present invention. FIG. 2 is a structural diagram of the imaging system according to the present invention.

As shown in FIG. 1, an object to be inspected moves between a radiation source A and a detector along a straight line. During the process of movement, the radiation source A emits radiations according to commands from a control system, which penetrates the object to be inspected. The detector receives transmitted signals, acquires projection data under the control of the control system, and stores the projection data into a memory.

The imaging system as shown in FIG. 2 comprises: a radiation source 110, which is for example an X ray accelerator, an X ray tube or a radioisotope source etc., and chosen according to the size of an object 120 to be inspected and the application environment; a transporting device 130, for carrying and transporting the object 120 to be inspected stably, and making the object to be inspected moving along a straight line; a detector array 140, which comprises a plurality of detector elements, is arranged opposite to the radiation source 110 and is vertical to the transporting device 130, and has a horizontal range of projection angle more than 90 degree relative to the radiation source 110, for example between 90 and 180 degrees, and covers the object in vertical direction, can be an planner detector or a collinear detector; a control and data signal bus 150, for transmitting control and data signals; and a controlling and image processing unit 160 connected to the radiation source 110, the transporting device 130 and the detector array 140, which controls the transporting device 130 to move along a straight line and commands the radiation source 110 to emit radiations, controls the detector array 140 to receive transmitted signals and generate the projection data, and performs post-processes to the generated projection data.

Therefore, the object 120 to be inspected moves uniformly according to the straight-line scan trajectory shown in FIG. 1, and the detector array 140 samples synchronously and with a constant time interval to obtain the projection data.

Figure 3:
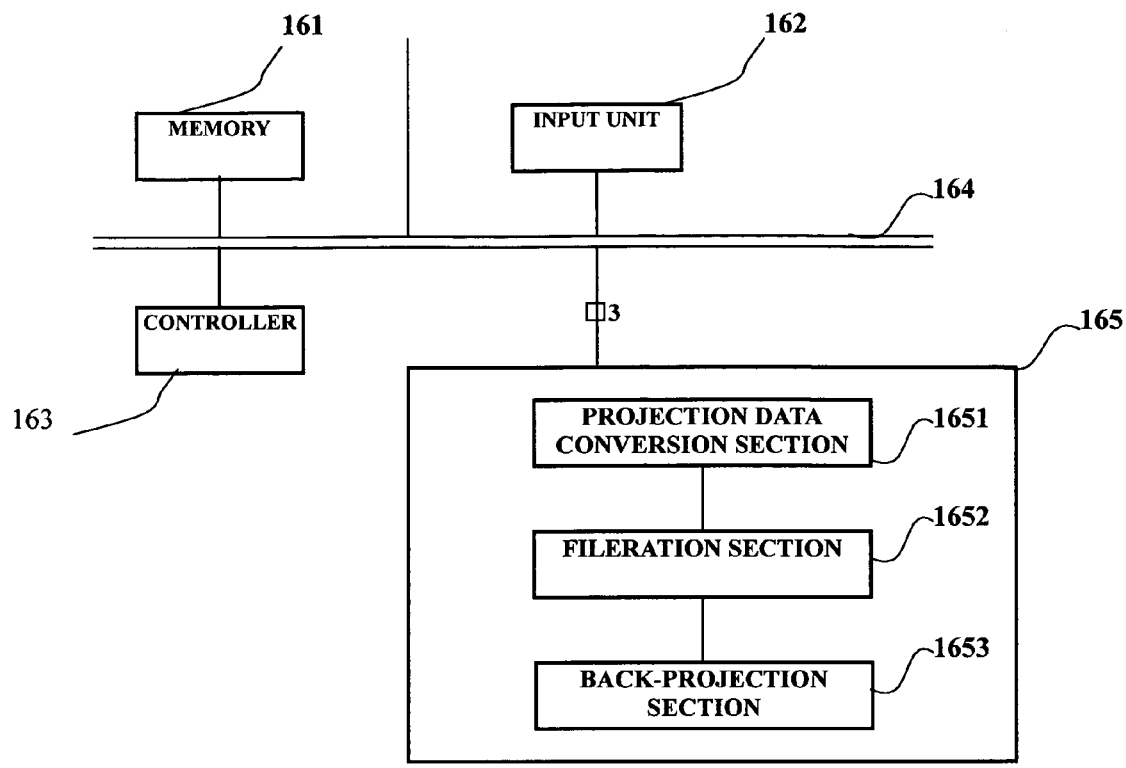
FIG. 3 is a functional block diagram of the controlling and image processing unit in the imaging system shown in FIG. 2.

FIG. 3 is a functional block diagram of the controlling and image processing unit 160 in the imaging system shown in FIG. 2. As shown in FIG. 3, the controlling and image processing unit 160 includes a memory 161 which is a storage medium such as hard disk and the like for storing data; an input unit 162 which is an input means such as keyboard for facilitating users to input parameters or commands; a controller 163 for, after the user inputs a command through the input unit 162, instructing the transporting unit 130 to make the object 120 to be inspected moving uniformly along a straight line, and the radiation generating unit 110 and data acquiring unit 140 to start working in order to obtain the projection data; an internal bus 164 for connecting each units and transmitting the control signals and data; and an image reconstruction unit 165 for performs reconstruction on the projection data obtained by the data acquiring unit 140.

Figure 4:
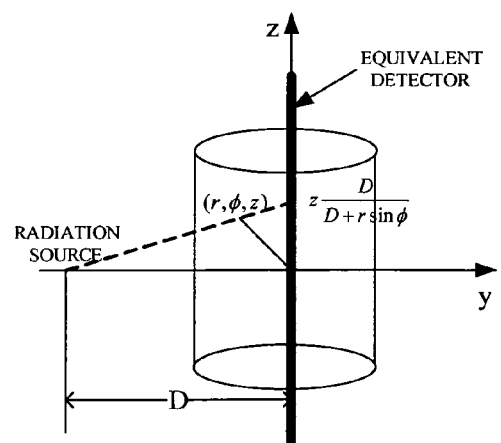
FIG. 4 is a schematic diagram showing the geometric relationship between the equivalent detector and the object point to be reconstructed in the Z direction.

The image reconstruction process will be described in detail with reference to FIG. 4. FIG. 4 is a schematic diagram showing the geometric relationship between the equivalent detector (the real detector is imaged onto the central line of the linear movement of the object) and the point of reconstructed object in Z direction.

Assuming that an approximate estimation for the object function $f(r,\phi,z)$ to be inspected is denoted as $\hat{f}(r,\phi,z)$, then the following equation is hold:

$$\hat{f}(r, \phi, z) = \int_{-t_m}^{t_m} \frac{1}{\sqrt{D'^2 + t^2}} Q\left(l', t, z\frac{D}{D + r\sin\phi}\right) dt \quad (1)$$

wherein, $$Q(l', t, z) = \int q(l, t, z) h(l' - l) dl \quad (2\text{-}1)$$

$$q(l, t, z) = p(-l + t, t, z) \quad (2\text{-}2)$$

$$l' = -r\cos\phi + \frac{tr\sin\phi}{D} \quad (3)$$

$$D' = \sqrt{D^2 + \left(z\frac{D}{D + r\sin\phi}\right)^2} \quad (4)$$

Here, the detector elements in the detector matrix are arranged with a constant spacing interval, and the data $p(l,t,z)$ denotes a projection value at a coordinate of t in the $z^{th}$ slice of the detector matrix when the object 120 to be inspected moves to a coordinate of l on the line. It should be noted that t and z are both equivalent values of each detector element of the detector matrix onto the central line of the linear movement of the object.

In addition, in Equations (1)-(4), D denotes a distance from the radiation source in the radiation generating unit 110 to the central line of the linear movement; $\pm t_m$ represent a minimum and a maximum positions of the detector matrix in the X-axis direction; h is a convolutional kernel, and its theoretical value is $$h(l) = \int_{-\infty}^{\infty} |\omega| e^{j2\pi\omega l} d\omega,$$

generally, an S-L type kernel is used, a discrete form of this kernel is:

$$h(n) = \frac{-2}{\pi^2(4n^2 - 1)}, n = 0, \pm 1, \pm 2, \ldots \quad (5)$$

Therefore, in the image reconstruction unit 165, a projection data conversion section 1651 reverses and shifts the projection data $p(l,t,z)$ to obtain $q(l,t,z)$, wherein $q(l,t,z)$ denotes projection data under quasi-parallel-beam scan. The meaning of the term "quasi-parallel-beam scan" is that for respective angles, the equivalent sampling intervals of the detector elements are different, and the scanned angular samples may not uniform either.

Thereafter, a filtration section 1652 performs one-dimension convolution of the projection data $q(l,t,z)$ under quasi-parallel-beam scan with the convolutional kernel h in the l direction to obtain filtered projection data $Q(l',t,z)$.

Next, a back-projection section 1653 back-projects the filtered projection data $Q(l',t,z)$ with a weighting factor along the radiation projection direction to obtain the reconstructed image.

Here, it should be noted that the object of reversing and shifting is to convert the projection data from a straight-linear trajectory scan into the projection data under quasi-parallel-beam scan. The quasi-parallel-beam scan is not the parallel-beam scan in a standard CT because for each of the respective angles, the equivalent sampling intervals of the detector elements are different, and the angular samples may not uniform either.

In addition, the object of filtration with the convolutional kernel h is the same as in a standard FBP (filtered back-projection) reconstruction algorithm, the reconstruction image can be achieved from the filtered projection data $Q(l',t,z)$ after weighted back-projection.

Therefore, in the present invention, the filtration is performed in the data acquiring direction l, and the back-projection is performed in the radiation projection direction. As compared with an algorithm of rebinning-to-parallel-beam and do standard parallel-beam FBP, the present invention can fully utilize each of the valid data, improves the image spatial resolution, and is less sensitive to data truncation than the rebinning-to-parallel-beam algorithm.

Figure 5:
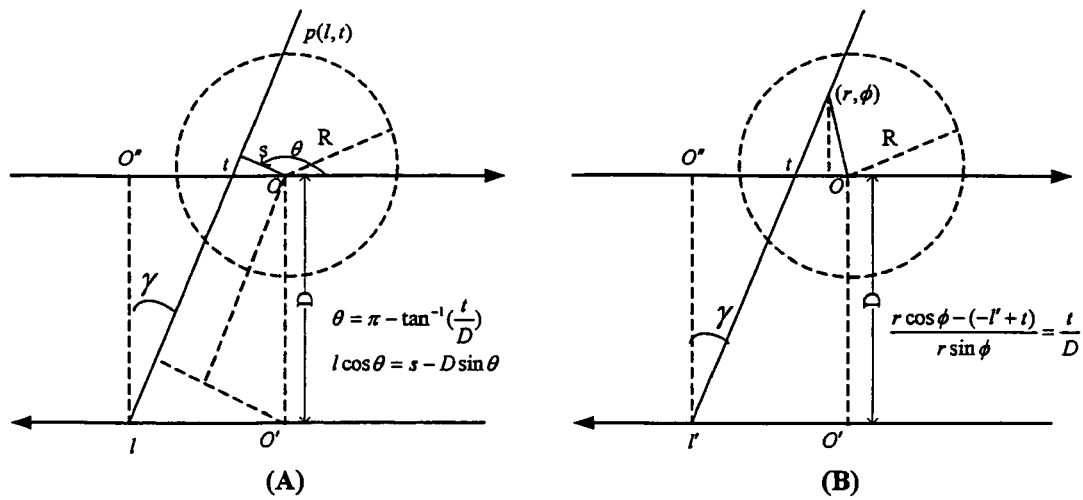
FIG. 5 is a schematic diagram for explaining the geometric relationship of the straight-line filtered back-projection procedure according to the present invention.

Below, the above Equation (1) will be derived by referring to FIGS. 1, 4 and 5. Before derivation, a procedure is firstly described for rebinning the linear scanned data into parallel-beam scanned data.

According to the scan mode shown in FIG. 1, each detector corresponds to one projection angle, and while the object $f(x,y)$ is moving, is equivalent to a parallel-beam scan under that angle. Referring to the projecting schematic diagram of FIG. 5, with respect to the detector matrix arranged with a constant spacing interval, the rebinning-to-parallel-beam formula for rebinning the linear scanned data into parallel-beam scanned data is:

$$g(\theta, s) = p(l, t) \Big|_{\substack{\theta = \pi - \tan^{-1}(\frac{t}{D}) \\ s = \frac{D(-l+t)}{\sqrt{D^2 + t^2}}}} \quad (6)$$

Here, $$g(\theta, s) = \int\int f(x, y) \delta(x\cos\theta + y\sin\theta - s) dx\,dy$$

represents projection data with a projection angle of $\theta$ and a distance from a rotation center of s in the parallel-beam scan. $p(l,t)$ denotes projection data in the detector array when the object to be inspected relatively moves to a coordinate of l on the line.

With Equation (6), it can be achieved to rebin the straight-line trajectory scanned projection data into the projection data under the parallel-beam scan. However, in practical systems, since an infinite straight line is impossible, the rebinned data is not the parallel-beam scanned data of 180 degree of projection angles. That is to say, the data are incomplete for exact reconstruction.

With respect to straight-line trajectory scan, although the samplings to l and t may be uniform, both the samplings of projection angle θ and detector's position s under the corresponding parallel-beam scan are not uniform. Therefore, the rebinning procedure requires interpolations in the angular direction and the detector direction, which results in degrading the spatial resolution of the reconstruction.

Next, the reconstruction process of direct filtration and back-projecting the linear scanned data according to the present invention will be described.

The reconstruction formula of filtered back-projection under the parallel beam scan is:

$$f(r,\phi) = \int_0^\pi \int_{-s_m}^{s_m} g(\theta, s) h(r\cos(\theta - \phi) - s) ds d\theta \tag{7}$$

Considering infinite straight-line trajectory and equidistantly spaced detectors, using Equation (7), (θ,s) is replaced by (l,t) so that:

$$f(r,\phi) = \int_{-\infty}^{\infty} \int_{-\infty}^{\infty} \frac{1}{\sqrt{D^2 + t^2}} p(-l+t, t) h(l' - l) dl dt \tag{8}$$

Here, $l' = -r\cos\phi + \frac{tr\sin\phi}{D}$.

It is demonstrated as follows:

$$f(r,\phi) = \int_\infty^{-\infty} \int_\infty^{-\infty} g\left(\pi - \tan^{-1}\left(\frac{t}{D}\right), \frac{D(-l+t)}{\sqrt{D^2+t^2}}\right) \cdot \tag{9}$$

$$h\left(r\cos\left(\pi - \tan^{-1}\left(\frac{t}{D}\right) - \phi\right) - \frac{D(-l+t)}{\sqrt{D^2+t^2}}\right) \frac{D^2}{(D^2+t^2)^{3/2}} dl dt$$

Here, $$\theta = \pi - \tan^{-1}\left(\frac{t}{D}\right), s = \frac{D(-l+t)}{\sqrt{D^2+t^2}}, ds d\theta = \frac{D^2}{(D^2+t^2)^{3/2}} dl dt.$$

In the straight-line trajectory scan, $$g\left(\pi - \tan^{-1}\left(\frac{t}{D}\right), \frac{D(-l+t)}{\sqrt{D^2+t^2}}\right)$$

is replaced by p(l,t). Also, according to the geometric structure of FIG. 5, the following results can be obtained:

$$r\cos\left(\pi - \tan^{-1}\left(\frac{t}{D}\right) - \phi\right) - \frac{D(-l+t)}{\sqrt{D^2+t^2}} = -r\cos\phi \frac{D}{\sqrt{D^2+t^2}} + \tag{10}$$

$$r\sin\phi \frac{t}{\sqrt{D^2+t^2}} - \frac{D(-l+t)}{\sqrt{D^2+t^2}}$$

$$= \left(l' - \frac{tr\sin\phi}{D} - t\right)\frac{D}{\sqrt{D^2+t^2}} +$$

$$r\sin\phi \frac{t}{\sqrt{D^2+t^2}} - \frac{D(-l+t)}{\sqrt{D^2+t^2}}$$

$$= \frac{D}{\sqrt{D^2+t^2}}(l' + l - 2t)$$

Here, $$l' = -r\cos\phi + \frac{tr\sin\phi}{D} + t,$$

which represents a space sampling position of the projection data passing through a point of (r,φ) and the $t^{th}$ detector element in the linear scan.

By substituting Equation (10) into Equation (9), using an equation $$h\left[\frac{D}{\sqrt{D^2+t^2}}(l'+l-2t)\right] = \frac{D^2+t^2}{D^2} h(l'+l-2t),$$

and substituting l=l–t, l'=l'–t, then the reconstructing formula (8) is achieved.

For Equation (8), if q(l,t)=p(–l+t,t) is substituted into Equation (8), then $$f(r,\phi) = \int_{-\infty}^{\infty} \frac{1}{\sqrt{D^2+t^2}} Q(l', t) dt \tag{11}$$

Here, $Q(l', t) = \int q(l, t) h(l' - l) dl.$

Actually, if the range of the straight-line trajectory is [–L, L] and the coverage of the detector is [–$t_m$, $t_m$], then the image reconstructed according to Equation (8) is not a f(x,y) exactly but only an approximate one. Further more, if a three-dimension situation is considered, then the approximate estimation f(r,φ,z) of the object f(x,y,z) to be inspected can be expressed by Equation (1).

Figure 6:
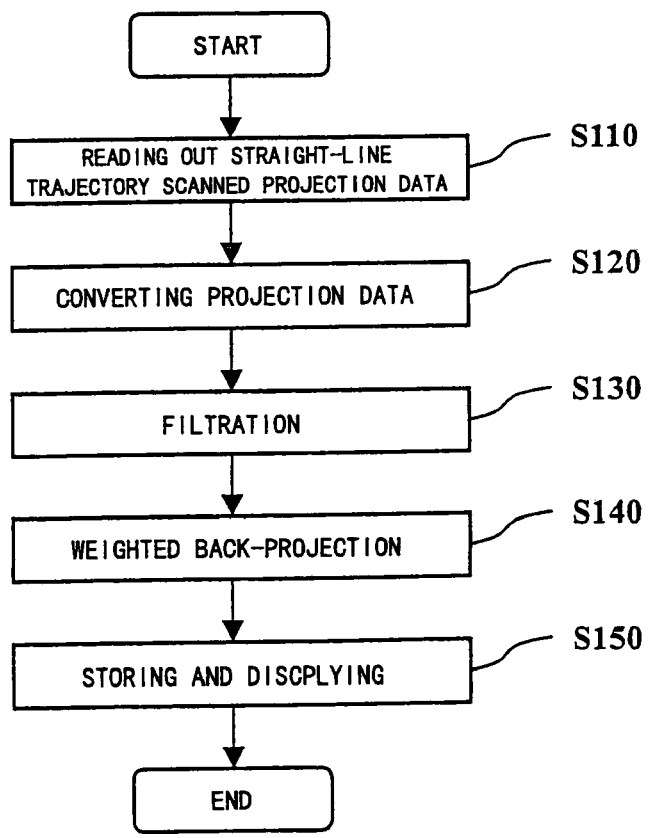
FIG. 6 is a flowchart of the straight-line filtered back-projection method according to the present invention.

FIG. 6 shows a flowchart of the straight-line filtered back-projection method according to the present invention. As shown in FIG. 6, after the detector matrix 140 obtains the projection data and stores these data in the memory 161, when an image is to be reconstructed, at step S110, the straight-line trajectory scanned projection data p(l,t,z) are read from the memory.

Then, at step S120, the projection data conversion section 1651 reverses and shifts the projection data p(l,t,z) to obtain q(l,t,z), wherein q(l,t,z) denotes projection data under quasi-parallel-beam scan.

Thereafter, at step S130, the filtration section 1652 does one-dimension convolution of the projection data q(l,t,z) under quasi-parallel-beam scan with the convolutional kernel h in the l direction to obtain filtered projection data Q(l',t,z).

Next, at step S140, the back-projection section 1653 back-projects the filtered projection data Q(l',t,z) with a weighting factor along the radiation projection direction to obtain the reconstructed image.

At step S150, the reconstructed image is stored in the memory 161 or displayed on a screen of a display 170.

Above, the filtration, back-projection and reconstruction formula (1) of the straight-line trajectory scan and the inventive image reconstruction method in a case of equidistantly spaced detector element arrangement are derived. Actually, the detector elements in the detector array can also be equi-angularly arranged. If the detector elements are arranged equi-angularly, similar to the above derivation, the filtration, back-projection and reconstruction formula can be changed to be:

$$\hat{f}(r, \phi, z) = \int_{-\gamma_m}^{\gamma_m} \frac{1}{\cos\gamma} Q\left(l', \gamma, z\frac{D}{D + r\sin\phi}\right) d\gamma \quad (12)$$

wherein, $$Q(l', \gamma, z) = \int q(l, \gamma, z) h(l' - l) dl \quad (13)$$

$$q(l, \gamma, z) = p(-l + D\tan\gamma, \gamma, z) \quad (14)$$

$$l' = -r\cos\phi + r\sin\phi\tan\gamma \quad (15)$$

Here, the detector elements in the detector matrix are arranged equi-angularly, and the data p(l,γ,z) denotes a projection value at an angular position of γ in the $z^{th}$ slice of the detector matrix when the object 120 to be inspected moves to a coordinate of l on the line. It should be noted that γ and z are both equivalent values of the detector matrix onto the central line of the linear movement of the object. The notation $\pm\gamma_m$ represent a minimum and a maximum angles of the detector matrix in the X-axis direction.

Therefore, in a case of equi-angularly spaced detector elements, the straight-line filtration, back-projection and reconstruction procedure is as above, in which the reversing and shifting operation is performed according to Equation (14), the meaning of the convolution operation is the same as that in the equidistance case.

In other words, in the projection data conversion section 1651, the projection data p(l,γ,z) are reversed and shifted to obtain q(l,γ,z), wherein the projection data p(l,γ,z) denotes a projection value at an angular position of γ in the $z^{th}$ slice of the detector matrix when the object to be inspected relatively moves to a coordinate of l on the line.

In the filtration section 1652, the projection data q(l,γ,z) under quasi-parallel-beam scan are one-dimensionally con-voluted with the convolutional kernel h in the l direction to obtain filtered projection data Q(l',γ,z).

In the back-projection section 1653, the filtered projection data Q(l',t,z) are back-projected with a weighting factor along the radiation projection direction to obtain the reconstructed image.

In order to precisely reconstruct images, the radiographic system shall be able to precisely measure or scale the following system parameters: a distance T from the radiation source to the detector matrix; a distance D from the radiation source to a central line of the linear movement; a linear movement speed v of the transporting unit; a sampling time interval Δt of the detector matrix; physical sizes of the detector including physical sizes of a single detector element and physical sizes of the detector matrix and the like.

Figure 7:
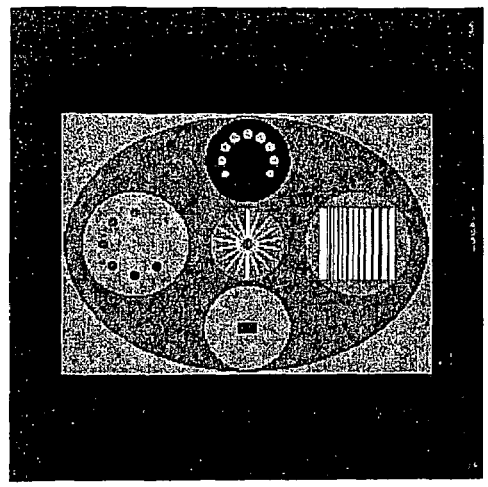
FIG. 7 is a performance comparison among numerical stimulated images (X-Y plane) obtained by reconstructing the data acquired by the stereoscopic imaging system with the inventive method and the rearranging parallel-beam method.
Figure 7:
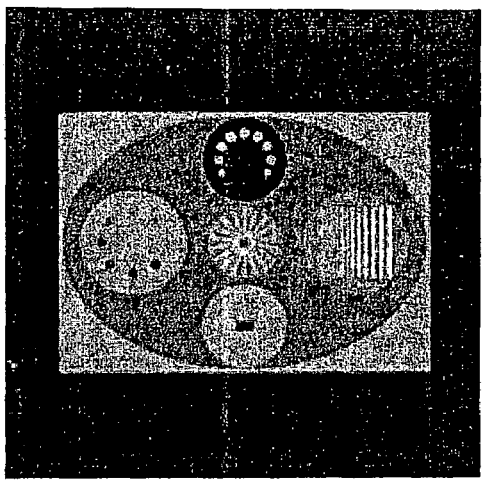
Figure 7:
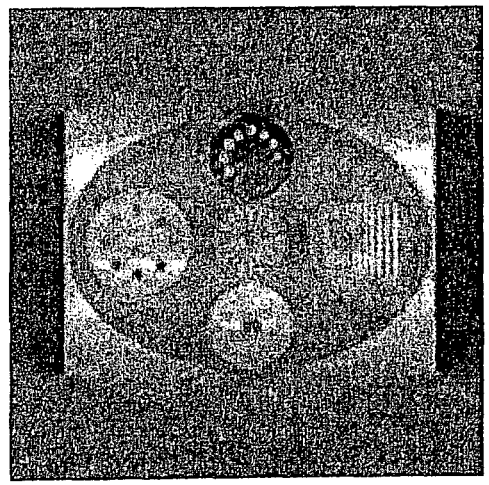
Figure 7:
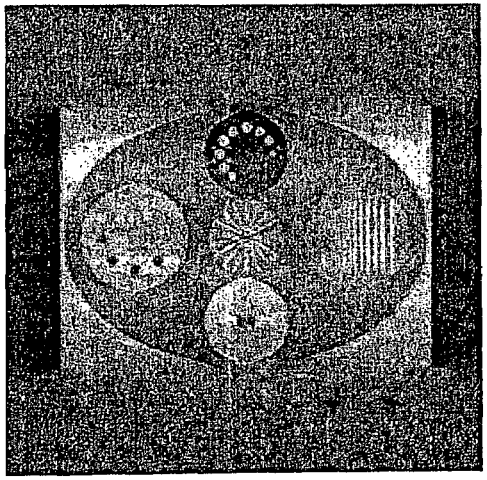
Figure 7:
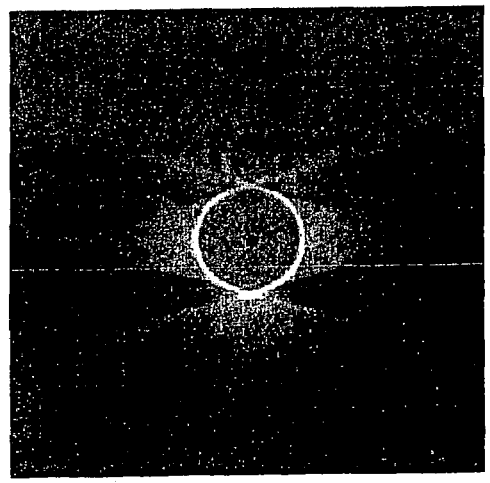
Figure 7:
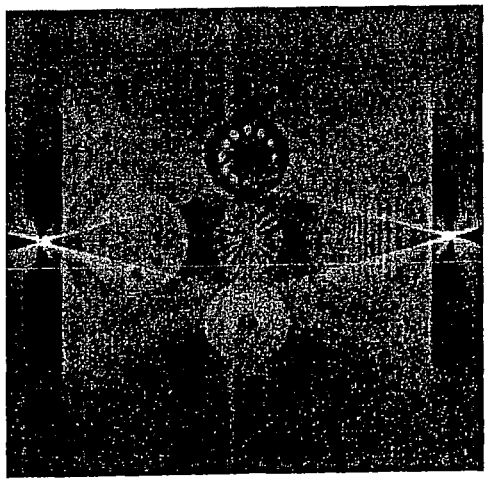

FIG. 7 is a performance comparison among stimulated tomographic images (X-Y plane) obtained by reconstructing the data acquired by the imaging system with the inventive method and the rebinning-to-parallel-beam algorithm, wherein a range of 150 degree of horizontal projection angles is chosen. The detector element has a width of 6 mm and are arranged equidistantly. The equivalent space sampling interval of the detector array is 3 mm. The reconstructed image is of 300*300 pixels, and each pixel has a size of 3 mm*3 mm. This figure is the stimulated results using a luggage model, in which the central slice is reconstructed, wherein (A) represents an original image of the model, (B) represents a exact reconstructed image by the parallel-beam scan, (C) represents an image reconstructed from the straight-line trajectory scanned projection data with the rebinning-to-parallel-beam method, (D) represents an image reconstructed with the inventive method, (E) represents another image reconstructed by the rebining-to-parallel-beam method in a case of data truncation in the detector direction, and (F) represents another image reconstructed by the inventive method in a case of data truncation in the detector direction. As shown in FIG. 7, the inventive method, as compared with the rebinning-to-parallel-beam method, significantly improves the spatial resolution, and reduces the influence of data truncation.

Hereto, the present invention has already been described with the preferred embodiments thereof. It should be understood by those skilled in the art, many variations, substitutions and additions are possible without departing from the spirits and scopes of the present invention. Therefore, the scopes of the invention should not be construed to be limited to the above specific embodiments but should be limited by the appended claims.

What is claimed is:

1. A system for reconstructing an image by using a straight-line trajectory scan, comprising:
    a projection data conversion section for converting projection data from straight-line trajectory scan into projection data under quasi-parallel-beam scan;
    a filtration section for obtaining filtered projection data by convoluting the projection data under quasi-parallel-beam scan with a predetermined convolutional kernel; and
    a back-projection section for reconstructing an image by back-projecting the filtered projection data with a weighting factor.

2. The system for reconstructing an image according to claim 1, further comprising: a detector matrix comprising a plurality of detector elements for receiving transmitted signals caused by radiations which are emitted from a radiation source and penetrate through an object to be inspected, and for converting the transmitted radiations into the projection data.

3. The system for reconstructing an image according to claim 2, wherein the plurality of detector elements are equilinear spaced.

4. The system for reconstructing an image according to claim 3, wherein:
the projection data conversion section reverses and shifts the projection data p(l,t,z) to obtain the projection data q(l,t,z) under quasi-parallel-beam scan, wherein the projection data p(l,t,z) denotes a projection value at a coordinate of t in the $z^{th}$ slice of the detector matrix when the object to be inspected relatively moves to a coordinate of l on the line;
the filtration section performs one-dimension convolution of the projection data q(l,t,z) under quasi-parallel-beam scan with the predetermined convolutional kernel in the l direction to obtain the filtered projection data Q(l',t,z); and
the back-projection section back-projects the filtered projection data Q(l',t,z) with a weighting factor along the radiation projection direction to obtain the reconstructed image.

5. The system for reconstructing an image according to claim 2, wherein the plurality of detector elements are equilangular spaced.

6. The system for reconstructing an image according to claim 5, wherein:
the projection data conversion section reverses and shifts the projection data p(l,γ,z) to obtain the projection data q(l,γ,z) under quasi-parallel-beam scan, wherein the projection data p(l,γ,z) denotes a projection value at an angular position of γ in the $z^{th}$ slice of the detector matrix when the object to be inspected relatively moves to a coordinate of l on the line;
the filtration section performs one-dimension convolution of the projection data q(l,γ,z) under quasi-parallel-beam scan with the predetermined convolutional kernel in the l direction to obtain the filtered projection data Q(l',γ,z); and
the back-projection section back-projects the filtered projection data Q(l',γ,z) with a weighting factor along the radiation projection direction to obtain the reconstructed image.

7. A method for reconstructing an image by using a straight-line trajectory scan, comprising:
a projection data conversion step for converting projection data from straight-line trajectory scan into projection data under quasi-parallel-beam scan;
a filtration step for obtaining filtered projection data by convoluting the projection data under quasi-parallel-beam scan with a predetermined convolutional kernel; and
a back-projection step for reconstructing an image by back-projecting the filtered projection data with a weighting factor.

8. The method for reconstructing an image according to claim 7, further comprising a step of:
receiving transmitted signals caused by radiations which are emitted from a radiation source and penetrate through an object to be inspected and converting the transmitted radiations into the projection data by a detector matrix including a plurality of detector elements.

9. The method for reconstructing an image according to claim 8, wherein the plurality of detector elements are equilinear spaced.

10. The method for reconstructing an image according to claim 9, wherein:
at the projection data conversion step, reversing and shifting the projection data p(l,t,z) to obtain the projection data q(l,t,z) under quasi-parallel-beam scan, wherein the projection data p(l,t,z) denotes a projection value at a coordinate of t in the $z^{th}$ slice of the detector matrix when the object to be inspected relatively moves to a coordinate of l on the line;
at the filtration step, performing one-dimension convolution of the projection data q(l,t,z) under quasi-parallel-beam scan with the predetermined convolutional kernel in the l direction to obtain the filtered projection data Q(l',t,z); and
at the back-projection step, back-projecting the filtered projection data Q(l',t,z) with a weighting factor along the radiation projection direction to obtain the reconstructed image.

11. The method for reconstructing an image according to claim 8, wherein the plurality of detector elements are equilangular spaced.

12. The method for reconstructing an image according to claim 11, wherein:
at the projection data conversion step, reversing and shifting the projection data p(l,γ,z) to obtain the projection data q(l,γ,z) under quasi-parallel-beam scan, wherein the projection data p(l,γ,z) denotes a projection value at an angular position of γ in the $z^{th}$ slice of the detector matrix when the object to be inspected relatively moves to a coordinate of l on the line;
at the filtration step, performing one-dimension convolution of the projection data q(l,γ,z) under quasi-parallel-beam scan with the predetermined convolutional kernel in the l direction to obtain the filtered projection data Q(l',γ,z); and
at the back-projection step, back-projecting the filtered projection data Q(l',γ,z) with a weighting factor along the radiation projection direction to obtain the reconstructed image.

* * * * *